US005455219A

United States Patent [19]
Trujillo

[11] Patent Number: 5,455,219
[45] Date of Patent: * Oct. 3, 1995

[54] **BIOLOGICAL CONTROL OF KNAPWEED BY *PYTHIUM ROSTRATUM***

[75] Inventor: Eduardo E. Trujillo, Honolulu, Hi.

[73] Assignee: Confederated Tribes of the Colville Reservation, Nespelem, Wash.

[ * ] Notice: The portion of the term of this patent subsequent to May 12, 2009 has been disclaimed.

[21] Appl. No.: 161,857

[22] Filed: Dec. 3, 1993

Related U.S. Application Data

[63] Continuation of Ser. No. 854,249, Mar. 20, 1992, abandoned, which is a continuation of Ser. No. 480,479, Feb. 14, 1990, Pat. No. 5,112,381.

[51] Int. Cl.$^6$ .............................. A01N 63/04; C12N 1/14
[52] U.S. Cl. ......................................... 504/117; 435/254.1
[58] Field of Search ............................................... 504/117

[56] References Cited

U.S. PATENT DOCUMENTS

| | | | |
|---|---|---|---|
| 3,179,653 | 4/1965 | Sherwood | 260/210 |
| 4,273,571 | 6/1981 | Berg et al. | 71/79 |
| 4,419,120 | 12/1983 | Walker | 71/79 |
| 4,755,208 | 7/1988 | Riley et al. | 71/79 |
| 4,929,270 | 5/1990 | Cardellina et al. | 71/92 |
| 5,112,381 | 5/1992 | Trujillo | 71/79 |

OTHER PUBLICATIONS

Miller, Patrick M. "V-8 juice agar . . . for fungi and bacteria." *Phytopath.* 45(8):461–2. 1955. *Biological Abstracts* 30: 17763.

Stierle et al, "Maculosin, a Host Specific Phytotoxin for Spotted Knapweed from *A. alternata,*" *Proc. Nat'l Acad. Sci.* U.S.A. 85: 8008–8011, 1988.

Stierle et al., "Phytotoxins from *A. alternata,* a pathogen of spotted knapwood," *J. Natural Products* 52:42–47, J.–F. 1989.

Templeton et al., "Progress and Potential of Weed Control with Mycoherbicides," *Rev. of Weed Sci.* 2:1–14, 1986.

Agrios, G. *Plant Pathology* 3rd ed. Ac. Pr. pp. 269–270, 292–299. 1988.

Schroeder, D., "The Search for Effective Biological Control Agents in Europe," in Ernest S. Delfosse (ed.), *Proc. of VI International Symposium on Biological Control of Weeds,* Agriculture Canada, 1984, pp. 103–119.

Butler, E. J., *Memoirs of the Department of Agriculture in India* 1(5):1–160, 1907.

Middleton, John T., "Taxonomy, Host Range and Geographic Distribution of the Genus Pythium," *Mem. Torrey Bot. Club* 20:171 pp., 1943.

Loprieno, N. "Differential Response of *Schizosaccharomyces pombe* to Ethyl Methanesulfonate and Methyl Methanesulfonate," *Mutation Research* 3:486–493, 1966.

Watson, A. K. and A. J. Renney, "The Biology of Canadian Weeds," *Can. J. Plant Sci.* 54:687–701, 1974.

Dennett, C. W. and M. E. Stanghellini, "Genetic and Cytological Evidence for a Diploid Life Cycle in *Pythium aphanidermatum,*" *Genetics, Phytophatology* 67:1134–1141, 1977.

Van Der Plaats–Niterink, A. J., "Monograph of the Genus Pythium," *Studies in Mycology 21,* Centraalbureau voor Schmmecultures, Baarn, 240 pp., 1981.

(List continued on next page.)

Primary Examiner—S. Mark Clardy
Attorney, Agent, or Firm—Seed and Berry

[57] ABSTRACT

A biologically pure culture of *Pythium rostratum* is disclosed which produces zoosporangia which produce zoospores capable of killing knapweed. Also disclosed is a method for killing knapweed, comprising: (a) growing *Pythium rostratum* which selectively kills knapweed on a carrier saturated with a liquid nutrient capable of supporting *Pythium rostratum* growth and the production of zoosporangia; and (b) applying the *Pythium rostratum* carrier to knapweed-infested land under moisture and temperature conditions sufficient to support *Pythium rostratum* growth and zoospore release by the zoosporangia, such that the zoospores are produced which are capable of killing knapweed.

9 Claims, 6 Drawing Sheets

OTHER PUBLICATIONS

Bruckart, W. L. and J. W. Lorbeer, "Pythium Species Pathogenic to Onion Seedlings Grown on Organic Soils in New York," *Phytopathology* 72(5):469–475, 1982.

Hall, Robert, "Pythium root rot of white bean in Ontario," *Can. Journal of Plant Pathology* 5:239–244, 1983.

Kröber, Heinz, "Erfahrungen mit Phytophthora de Bary und Pythium Pringsheim," Biologische Bundesanstalt für Land– und Forstwietschaft, Institut für Mikrobiologie, Berlin–Dahlem, 225 pp., 1985.

Stanghellini, M. E. and W. C. Kronland, "Yield Loss in Hydroponically Grown Lettuce Attributed to Subclinical Infection of Feeder Rootlets by *Pythium dissotocum*," *Plant Disease* 70:1053–1056, 1986.

Roche, Jr. et al., "Knapweed Control in the Context of Land Management," *Knapweeds of Washington*, Washington State Coop. Ext. Serv. Ext. Bull. 1393, 41 pp. 1986.

Trujillo, E. E. and F. P. Obrero, *Cepahlosporium wilt of Cassia Surattensis in Hawaii*, pp. 217–220. 1976. Proceedings IV International Symp. on Bio. Control of Weeds, Gainesville, Fla.

BIOLOGICAL CONTROL OF KNAPWEED BY *PYTHIUM ROSTRATUM*

CROSS-REFERENCE TO RELATED APPLICATION

This application is a continuation of U.S. patent application Ser. No. 07/854,249, filed Mar. 20, 1992; now abandoned, which was a continuation of U.S. Ser. No. 07/480,479, filed Feb. 14, 1990, issued as U.S. Pat. No. 5,112,381.

TECHNICAL FIELD

The present invention relates generally to the biological control of knapweed and, more specifically, relates to isolates of *Pythium rostratum* and mutants thereof which are capable of selectively killing knapweed, and to methods of applying such organisms in the environment.

BACKGROUND OF THE INVENTION

Introduced weeds, such as diffuse knapweed, *Centaurea difussa* Lam., spotted knapweed, *C. maculosa* Lam., and yellow thistle, *C. solstitiales* Lam., are a major threat to range and croplands. Knapweed damages rangelands by overgrowing and smothering indigenous grasses, thus eliminating the basic foodstuff of grazing animals. Similarly, knapweed may also take over cropland, choking off or diminishing the potential harvest of commercially valuable crops.

Knapweed is in the genus Centaurea, which is in the Carduus tribe of the Compositae. The Compositae is a family of flowering broadleaf plants containing about 19,000 species. Many commercially valuable plants are found in the Compositae family, including, inter alia, safflower (Compositae/Carduus, *Carthamus tinctorius*), artichokes (Compositae/Carduus, *Cynara scolymus*); and lettuce (Compositae/Cichorium, *Lactuca sativa*). The commercial importance of many crops which are phylogenetically related to knapweed, and the large number of broadleaf plants in the Compositae family, make the control of knapweed difficult using traditional methods.

At least four methods have been used in an effort to control knapweed: (1) herbicides, (2) mechanical means, (3) hand pulling, and (4) biological means. Several herbicides are currently in use for the control of knapweed. 2,4-D (2,4-Dichlorophenoxy acetic acid) is effective for short-term control of knapweed. One disadvantage, however, is that because there is no residual effect of 2,4-D, applications are required several times in one season to effectively control knapweed. This is due to the large numbers of seeds produced by some knapweeds, which enables the population to be replaced within days. Another herbicide, Tordon 22K (Picloram™, Dow Chemical Co.), is a selective herbicide which also kills knapweed. It is advantageous because it has residual effectiveness for up to three years and thus can control knapweed for a significant period of time. It is unsuitable, however, because its use is restricted in or around open water. Herbicides which kill knapweed are generally disadvantageous because they affect a broad spectrum, killing many, if not all, broadleaf plants. Additionally, after aerial spraying many herbicides may travel into nearby fields, damaging other crops or nearby forestlands. Furthermore, some herbicides, like 2,4-D, release esters on warm days which are toxic to broadleaf plants within a three-mile radius of the treated land.

Mechanical means have also been used in an attempt to control knapweed. Such methods generally involve tilling of the soil by discing, plowing, or rotovating. One disadvantage of these methods, however, is that as soon as the soil receives moisture knapweed seeds will germinate and a more dense stand of knapweed will grow. Although pulling out knapweed by hand is effective because the plants can be pulled up by the roots and removed, it is extremely expensive and labor intensive in areas with dense knapweed populations. Further, even if the plant is removed, seeds remaining in the soil will germinate once the soil receives moisture.

Finally, biological control methods have been proposed for use in the control of knapweed. For instance, a number of different species of insects have been identified which infest and destroy knapweed. Although these insects are not as harmful to the environment as herbicides, they are relatively slow and ineffective, and the cost of propagating the insects is quite high. Additionally, enough seed may survive to maintain dense populations of knapweed even after a round of infestation by insects.

Contrary to the previously disclosed methods and agents used to control knapweed, the present invention provides for the effective and specific control of knapweed, as well as other related advantages.

SUMMARY OF THE INVENTION

Briefly stated, the invention provides a method for selectively killing knapweed comprising the steps of: (a) growing *P. rostratum* which selectively kills knapweed on a carrier saturated with liquid nutrient capable of supporting *P. rostratum* growth and the production of zoosporangia; and (b) applying the *P. rostratum* carrier to knapweed-infested land under moisture and temperature conditions sufficient to support *P. rostratum* growth and zoospore release by the zoosporangia, the zoospores being capable of killing knapweed. In one embodiment of the invention, the carrier comprises vermiculite, V8™ juice, and $CaCO_3$. It is preferred that the carrier be applied under moisture conditions of about 100% of soil capacity. It is also preferred that the carrier be applied under temperature conditions of about 8° C. to 18° C.

In another aspect of the invention, a biologically pure culture of *P. rostratum* is provided, having substantially the characteristics of ATCC No. 20976, the culture being capable of producing zoosporangia which produce zoospores capable of killing knapweed.

In yet another aspect of the invention, a biologically pure culture of *P. rostratum* has been mutagenized such that it produces no zoospores, the culture being capable of producing zoosporangia which produces zoospores capable of killing knapweed. In selected embodiments, biologically pure cultures of *P. rostratum* mutants PR4 and PR24 (Deposit Nos. 20977 and 20978, respectively) are provided.

In another aspect of the present invention, a composition suitable for application to knapweed infested land is provided, comprising: (a) a biologically pure culture of *Pythium rostratum*, the culture being capable of producing zoosporangia which produce zoospores capable of killing knapweed; and (b) a carrier saturated with a liquid nutrient capable of supporting *Pythium rostratum* growth and the production of zoosporangia.

In one embodiment, the biologically pure culture of *Pythium rostratum* has been mutagenized such that oospores are not produced. In another embodiment, the carrier comprises vermiculite, V8™ juice, and CaCO$_3$, preferably about 17% by weight vermiculite, about 82% by weight V8™ juice, and about 1% by weight CaCO$_3$.

These and other aspects will become evident upon reference to the following drawings and detailed description.

DETAILED DESCRIPTION OF THE INVENTION

Figure 1:
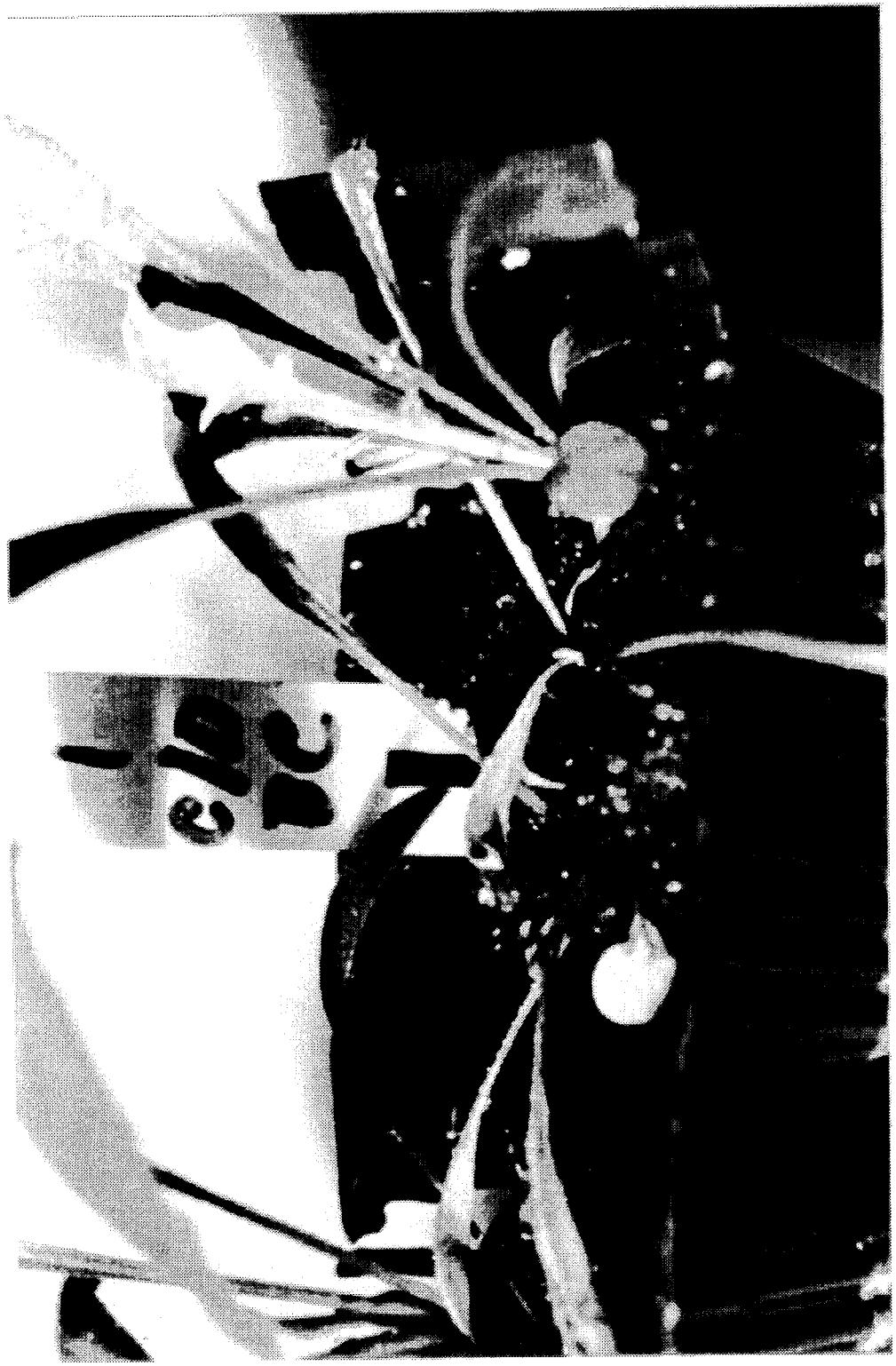
FIG. 1 is a photograph of diffuse knapweed seedlings showing damping-off symptoms caused by P. rostratum. The apical portions of the plants in the center have collapsed and rotted away.

As noted above, the present invention is directed toward P. rostratum which selectively kills knapweed and mutants of P. rostratum which selectively kill knapweed and produce no oospores. P. rostratum suitable for use with the present invention may be isolated by the method described below. Briefly, P. rostratum may be isolated from a diseased section of a knapweed plant. Diseased plants manifest symptoms ranging from wilting and yellowing of foliage to tip dieback, discoloration of the vascular system, root rot, and crown rot. The diseased section can be cultured for P. rostratum by burying pieces of the section into isolation media suitable for the growth of pathogens. A preferred media is water agar (20% agar in 1000 ml of water). After about 48 hours, one of ordinary skill in the an can then isolate colonies of P. rostratum using a stereo-microscope with base illumination. Potential pathogens such as P. rostratum will have grown away from the sample into the clear agar, thus allowing taxonomic identification and isolation of P. rostratum. P. rostratum Butler is taxonomically identified by the following characteristics:

Hyphae often large, measuring up to 6 to 8 μm in diameter. Sporangia are spherical to oval, terminal or intercalary, measuring 23 to 34 μm, average 28 μm, in diameter, usually appearing before sexual reproductive bodies; zoospores few to 40, 8 to 11 μm, average 9.6 μm, in diameter at encystment, formed in a vesicle arising from a large, stout evacuation tube usually equal to the diameter of the sporangium, frequently of lateral origin. Oogonia spherical to subspherical, typically intercalary, occasionally terminal measuring 13 to 29.4 μm, average 21 μm, in diameter. Antheridia typically monoclinous, infrequently hypogynal, single, rarely 2 per oogonium, the antheridial cell often extremely short, reduced to a lateral swelling, immediately below the oogonium, the antheridial cell sessile and not otherwise delimited, the whole forming the antheridium. Oospore plerotic, single, with a moderately thickened wall, measuring 12 to 27 μm, average 20 μm, in diameter; germination not observed. Originally described as saprophytic in garden soil France. Temperature requirements minimum 5° C., optimum 25° C., maximum 34° C. (2,3). (Buffer, Mem. Dept. Agric. India Bot. Ser. 1(5):1–160, 1907.)

In accordance with the above taxonomic characteristics, hyphal tips from mycelium which are non-septated and have produced spherical zoosporangia are transferred to media, resulting in the isolation of a biologically pure culture of P. rostratum.

Host range studies may be performed on a limited basis in order to determine the pathogenicity and specificity of the isolate for knapweed, as well as for other plants in the Compositae family. Plants may be grown for the host range studies from seed in sterilized sand irrigated with a nutrient solution, such as Hoaglund solution. Once the seedlings are about two weeks old, they may be inoculated with P. rostratum. P. rostratum may be grown in any media well known in the art which will support the growth of P. rostratum and production of zoosporangia. Twenty percent V8 agar is the preferred medium for the growth of P. rostratum and the production of zoosporangia. Once the culture has produced zoosporangia, and these have become mature, zoospores produced by the zoosporangia may be used for inoculation of seedlings. There are many methods known in the art for causing zoospores to be released from the zoosporangia. A preferred method is to place the zoosporangia in chilled water. Tap water at 16° C. is particularly preferred. Due to the temperature differential, after about 6–12 hours the zoosporangia will release the entire protoplasm into a vesicle where zoospores are formed. Zoospores encysted or swimming in the water are then applied to the crown of the seedlings. Alternatively, or in addition to the zoospores in water, an agar plug or culture disk from the V8 agar plate containing mature zoosporangia may be used to inoculate seedlings by placement of an agar plug near the roots of the seedlings.

Figure 2:
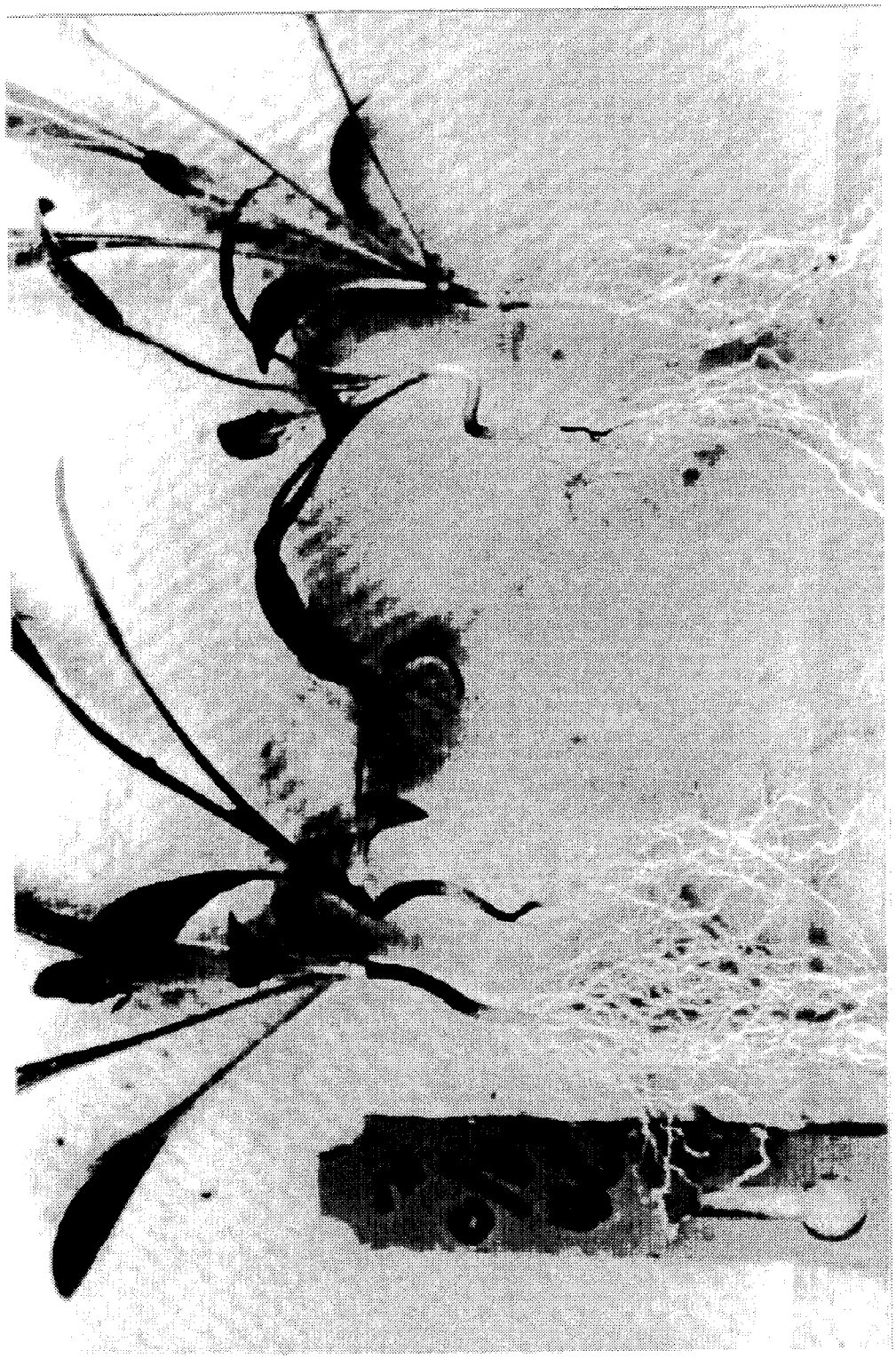
FIG. 2 is a photograph of Centaurea diffusa seedlings two weeks after inoculation with P. rostratum, the inoculated plants (left) showing wilting, black discoloration of the roots, and girdling of the crown. The plants on the fight are healthy.
Figure 3:
FIG. 3 is a photograph of a three-month-old C. diffusa four weeks after inoculation with P. rostratum, the inoculated plant (left) showing wilting of the foliage and necrosis of the apical shoot. Uninoculated, healthy plants are shown on the right.

The seedlings are then inspected for signs of disease. Dead plants are carefully examined, including the removal of the plant from the sand and an examination of any deteriorating aspect of the plants, such as the roots, crown, or stem. Disease symptoms caused by P. rostratum include the damping-off of young seedlings of spotted and diffuse knapweeds. Plants show a severe wilt about one week after inoculation; the stem becomes watery, soft, shriveled, and collapsed at the soil line (see FIG. 1). The roots show brown to black discoloration (see FIG. 2). In older plants, a dark brown crown rot girdling the taproot is common. Portions of the plant showed wilting and chlorosis of the lower leaves, and necrosis occurs once the plant is dead (see FIG. 3).

To ensure that P. rostratum was the causative agent of plant death, a specimen from the diseased plant may be isolated on 2% water agar. The hypal tips may then be transferred to 20% V8 agar medium and taxonomically identified.

Once a suitable isolate of P. rostratum has been identified it may be used within the methods described herein, or suitable mutants may be produced. Mutants that do not produce oospores are preferred. Mutants which lack oospore-producing capabilities may not be able to survive winter freezing and/or summer heating of soils, and thus are limited in their ability to spread to other regions and damage crops.

Many procedures are well known in the art for mutagenizing microorganisms, for example, UV or gamma irradiation, nitroso-guanidine, and methanesulfonic acid ethyl ester (EMS). EMS however, is the preferred mutagenizing agent because it is less toxic and does not kill all zoospores even though it is highly mutagenic. Zoospores which have been obtained from the mature zoosporangia using the above described methods may be treated with 5 μg/ml of EMS for about 15 minutes. It is generally preferred that only about 1% of the zoospores remain viable after treatment with EMS. Following treatment, the zoospores are plated onto a suitable medium, such as 2% clarified V8™ juice agar with an antibiotic which reduces bacterial growth, and yet allows *P. rostratum* to grow. Particularly preferred is 300 ppm Vancomycin. Viable zoospores which exhibit hyphal growth (approximately 1% of the original zoospore population) are then plated onto V8 agar, and non-oospore-forming colonies are isolated. Of the zoospores which exhibit hyphal growth, about 1% –2% of these will be mutated such that they can no longer produce oospores.

Host range studies are then performed in order to ensure that *P. rostratum* is strongly pathogenic for only knapweed and weakly pathogenic or nonpathogenic for most other members of the Compositae family. For these experiments, seedlings comprising representatives from all the tribes, as well as many genus and species of the Compositae, are grown under disease-free conditions. A protocol similar to the limited host range studies described above may then be followed for a more extensive cross-section of the Compositae, in order to ensure the specific pathogenicity of *P. rostratum* or mutant thereof for knapweed.

Once the specific pathogenicity and host range has been determined, the *P. rostratum* mutant or the initial *P. rostratum* isolate may be applied to fields infested with knapweed in order to destroy the knapweed. As discussed above, the *P. rostratum* mutant is generally preferred for field applications because it produces no oospores and thus may not survive over the winter. Representative mutants have been deposited under ATCC Nos. 20977, and 20978.

Application of *P. rostratum* is preferably accomplished by first preparing a carrier for *P. rostratum*. An inert material which can absorb large quantities of liquid nutrient is preferable as a carder. Examples of inert materials include Pearlite™, and vermiculite. The inert material should be saturated with a liquid nutrient which is capable of supporting the growth of *P. rostratum* and production of zoosporangia. Many such liquids are well known in the art, but V8™ juice (Campbell Soup Co.) is the preferred liquid nutrient. V8™ juice contains extracts of eight vegetables, and comprises the best known substrate for growing *P. rostratum*. Since V8™ is slightly acidic, an alkaline substance should be added to increase the pH into a range more conducive to the growth of *P. rostratum*. A range of pH from 6.4 to 6.6 is preferred. Many such alkaline substances are Well known in the art, although calcium carbonate ($CaCO_3$) is preferred because it provides a nontoxic substrate for *P. rostratum*, as well as serving to increase the pH.

The carrier which comprises the inert material impregnated with the liquid capable of supporting the growth of *P. rostratum* should then be sterilized by any number of nontoxic methods well known in the art, such as γ irradiation, dry heat, or steam sterilization. A culture of the previously isolated or mutagenized *P. rostratum* is then transferred to the sterilized carrier. The *P. rostratum* is grown on the carrier at temperatures conducive for growth and the production of zoosporangia. A preferred temperature is 25° C. *P. rostratum* should be grown on the carrier until a large number of zoosporangia is produced on the surfaces of the carrier. These zoosporangia may be seen by microscopic examination within about 20 days after the carrier has been inoculated with a culture of *P. rostratum*. Alternatively, the number of zoosporangia per gram of carrier may be determined by fragmenting a gram of carrier in a blender, and serially diluting the blended mixture such that the number of zoosporangia can be counted in a hemocytometer. Once the carrier has about 50,000 to 100,000 zoosporangia per gram, it may then be applied to knapweed infested land. Although it is preferred to apply the carrier once there are 50,000 to 100,000 zoosporangia per gram, the carrier may be stored for up to about 15 days before the carrier becomes ineffective due to dying zoosporangia.

The *P. rostratum* carrier is applied to knapweed-infested land when proper temperature and moisture conditions are present. Proper moisture and temperature conditions are those which support zoospore release by *P. rostratum* zoosporangia and the infection of knapweed by the zoospore. Soil moisture capacity may be determined using methods well known in the art. Generally, the moisture capacity of soil should be between the field capacity of the soil (–0.1 bars), and saturation of the soil (–0.001 bars) (see Falisbury and Ross, *Plant Physiology*, 3rd ed., pages 86–7, Wadsworth Publishing Co., Belmont, Calif., 1985). Particularly preferred are conditions where the soft is saturated to 100% of its capacity. These conditions may usually be found during seasons of heavy rain, or during the spring after snow melts. Alternatively, requisite moisture conditions may also be generated artificially by providing sufficient water to allow zoosporangia to germinate indirectly by zoospore release. About one inch of water per acre is generally preferred.

Proper temperatures must also be present in order for zoospores to form and be released. *P. rostratum* may be grown at any temperature known in the art which will support the growth of *P. rostratum* and zoosporangia production. Temperatures between 18° C. and 20° C. are generally preferred. For zoospore release temperatures between 8° C. and 18° C. are generally preferred.

Once the temperature and moisture considerations have been met, the carrier containing *P. rostratum* mycelium and zoosporangia may be applied to the field by any methods well known in the art, including aerial release, manual or mechanical spreaders. Given about 50,000 to 100,000 zoosporangia per gram of carrier, approximately 5 to 20 pounds per acre of inoculated carrier is applied to each acre of land. This results in a dispersion of 2600 to 20,800 zoosporangia per square foot of land. The actual amount of inoculated carrier to be applied is dependent on the degree of knapweed infestation on the land; dense stands of knapweed require greater amounts of the inoculated carrier.

Alternatively, as opposed to using a carrier, one may utilize a suspension of zoosporangia suitable for application to knapweed infested land. Briefly, a culture of *P. rostratum* is inoculated into media and provided sufficient aeration such that the *P. rostratum* will grow and form zoosporangia. Once the zoosporangia have formed a suspension, the suspension may be applied to knapweed infested fields under the above discussed moisture and temperature conditions, using any methods well known in the art.

The following examples are provided by way of illustration and not by way of limitation.

EXAMPLE 1

Isolation of P. rostratum

Areas of knapweed growth were located, and these areas were searched for diseased knapweed. Once diseased plants were identified, samples were removed from a diseased section of the plant, and buried in water agar (20% agar in 1000 ml of water). After about 48 hours, presumptive pathogens had grown away from the sample into the agar, and could be identified by their morphology and cultured into new plates. Putative pathogens such as P. rostratum could then be taxonomically identified.

EXAMPLE 2

Initial Pathogenicity Tests

Initial pathogenicity tests were performed to ensure that the isolate was in fact pathogenic to knapweed. P. rostratum (PR1) and P. debaryanum were selected for the initial pathogenicity tests.

Two-week-old seedlings of Compositae were used for pathogenicity studies. Seedlings were grown in quartz sand in 5-cm plastic pots (twelve pots per 22.23×16.65 cm sheet), placed in nonperforated flats of similar size, and irrigated as needed with Hoagland solution.

Ten-day-old P. rostratum and P. debaryanum V8 agar cultures about 0.6 cm in diameter and/or encysted zoospore suspensions were used for inoculations of the seedlings. P. rostratum and P. debaryanum were grown for 10 days at 20° C. on 20% V8 ™ juice agar plates with illumination of about 500 lux. The zoosporangia were then submerged in 10 ml of 16° C. tap water for 24 hours in order to release the zoospores. Additionally, plugs approximately 1cm² in diameter were removed from locations on the agar plate where mature zoosporangia were present.

Seedling inoculation was performed by irrigating sterilized sand culture pots with 10 ml of zoospore suspension, and by inserting the agar plugs in the wet sand about 1 cm deep and about 1 cm from the seedling. Seedlings were then put into a dew chamber for one week and kept at 18° C. Thereafter, the seedlings were moved into a green house and checked weekly for mortality. At the end of week 4, the plants were removed, and roots were examined for signs of disease. Additionally, the room which appeared to be diseased were cultured to identify the presence of P. rostratum. The following index rating was used to categorize the extent of disease:

0=no visible damage or root discoloration

1=slight discoloration and root damage

2=extensive root discoloration and/or crown lesions

3=root discoloration and girdling of plant at soil surface

4=death of plant

TABLE 1

Results of inoculations of different Composite with 2 Pythium species. Inoculated from 0.6 cm. diameter 9-day-old V8 culture disk and encysted zoospore suspensions. Data presented as No. of Dead/No. of either Inoculated or Uninoculated Plants. Incubated at 18° C. in an illuminated dew chamber.

| Host | P. rostratum Cult Disk | P. rostratum Zoospore | P. debaryanum Cult Disk | Control Water |
|---|---|---|---|---|
| Carthamus tinctorius | 5/6 | 4/6 | 0/6 | 0/6 |
| Centaurea calcitrapa | 1/6 | 5/6 | 0/6 | 0/6 |
| Centaurea cyanus | 6/6 | 6/6 | 0/6 | 0/6 |
| Centaurea diffusa | 6/6 | | 0/6 | 0/6 |
| Centaurea maculosa | 6/6 | 4/6 | 0/6 | 0/6 |
| Centaurea maculosa | 1/4 | 6/6 | 1/5 | 0/6 |
| Centaurea maculosa | 2/4 | | 0/5 | 0/6 |
| Centaurea melitensis | 1/6 | 1/6 | 0/6 | 0/6 |
| Centaurea solstidialis | 2/5 | 6/6 | 0/6 | 0/6 |
| Centaurea solstidialis | 4/6 | 5/6 | 0/6 | 0/6 |
| Centaurea squarrosa | 5/5 | | 1/5 | 0/6 |
| Centaurea sulphurea | 1/6 | 2/6 | 1/6 | 0/6 |

TABLE 2

Results of inoculations of different species of Composite with 10-day-old culture disk of P. rostratum. Inoculation = No. of Dead/No. of Inoculated Plants. Control = No. of Dead/No. of Uninoculated Plants.

| Host | Inoculated | Control |
|---|---|---|
| Carthamus tinctorius | 5/11 | 0/12 |
| Centaurea americana | 10/11 | 0/12 |
| Centaurea calcitrapa | 0/12 | 0/12 |
| Centaurea calcitrapa | 5/12 | 0/10 |
| Centaurea cyanus | 4/11 | 0/12 |
| Centaurea diffusa | 12/12 | 0/12 |
| Centaurea diffusa | 10/12 | 0/12 |
| Centaurea diffusa | 10/12 | 0/12 |
| Centaurea maculosa | 11/12 | 0/11 |
| Centaurea maculosa | 6/12 | 0/12 |
| Centaurea maculosa | 5/11 | 0/12 |
| Centaurea maculosa | 12/12 | 0/10 |
| Centaurea maculosa | 12/12 | 0/12 |
| Centaurea melitensis | 0/12 | 0/12 |
| Centaurea pathlagonica | 11/12 | 0/8 |
| Centaurea pathlagonica | 5/8 | 0/7 |
| Centaurea rothrockii | 1/12 | 0/8 |
| Centaurea solstitialis | 10/12 | 0/12 |
| Centaurea sulphurea | 2/12 | 0/12 |
| Centaurea scolymus | 3/12 | 0/12 |

Figure 4:
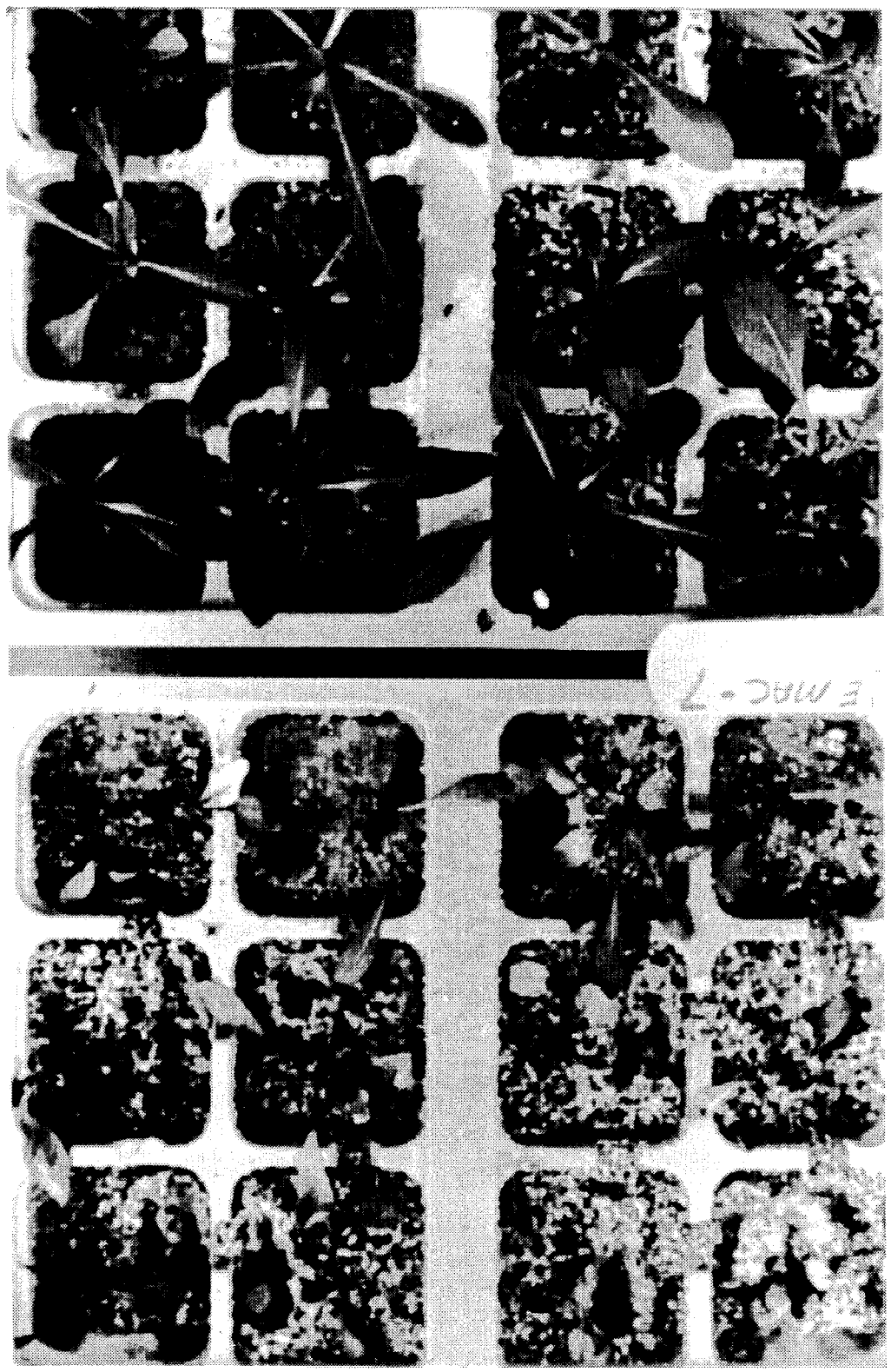
FIG. 4 is a photograph showing damping-off symptoms on Centaurea maculosa seedlings two weeks after inoculation with P. rostratum (left). Healthy seedlings (right) were inoculated with P. debaryanum.

In general, the results showed little difference in pathogenicity of P. rostratum (PR1) to Compositae, when zoospore suspension or the culture disk was used for inoculation (see Table 1). P. rostratum showed aggressive pathogenicity to Centaurea diffusa, C. maculosa, C. solstitialis, C. cyanus, C. calcitrapa, C. squarrosa, and Carthamus tinctorius. In contrast, Pythium debaryanum was either non-pathogenic or only weakly pathogenic for all of the plants (see also FIG. 4). P. rostratum (PR1) has been deposited with the ATCC under ATCC No. 20976.

EXAMPLE 3

Production of Pythium rostratum Mutants Lacking Oospores

The original isolate of P. rostratum (PR1), was used to produce biochemical mutants by treating zoospores in tap water with 5 mg/ml of methanesulfonic acid ethyl ester (EMS) for 15 minutes. EMS-treated zoospores were then placed on agar plates (2% clarified V8 ™ juice, 20% agar, and 300 ppm of Vancomycin) and grown for 48 hours at 18° C. Vancomycin at 300 ppm was added to suppress the bacterial flora commonly present in tap water, allowing single zoospores not killed by the EMS treatment to grow free of bacteria in the isolation medium. EMS at 5 mg/ml for 15 minutes killed more than 99% of the zoospores.

Figure 5:
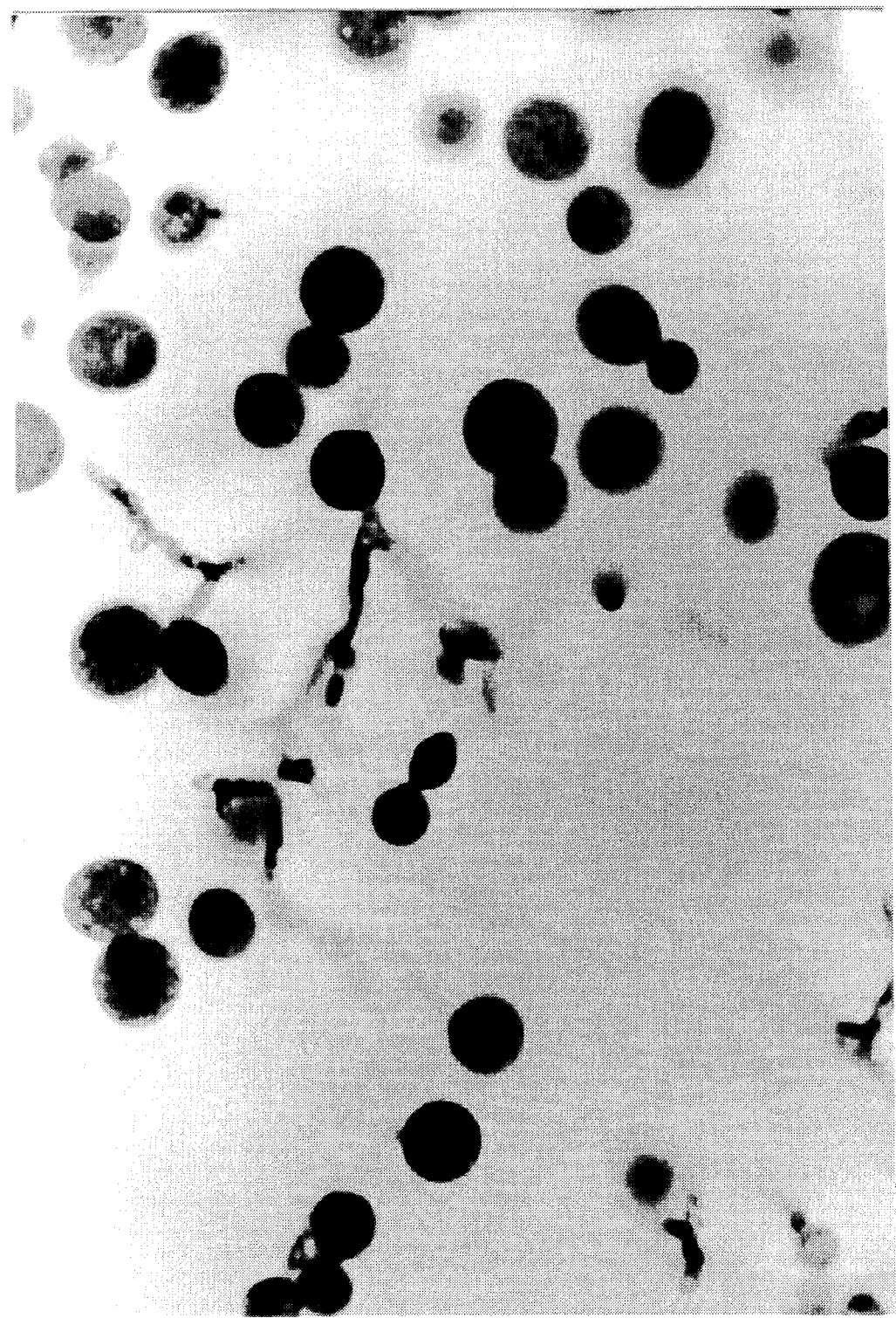
FIG. 5 is a photograph of the zoosporangia of biochemical mutant P. rostratum (PR24).
Figure 6:
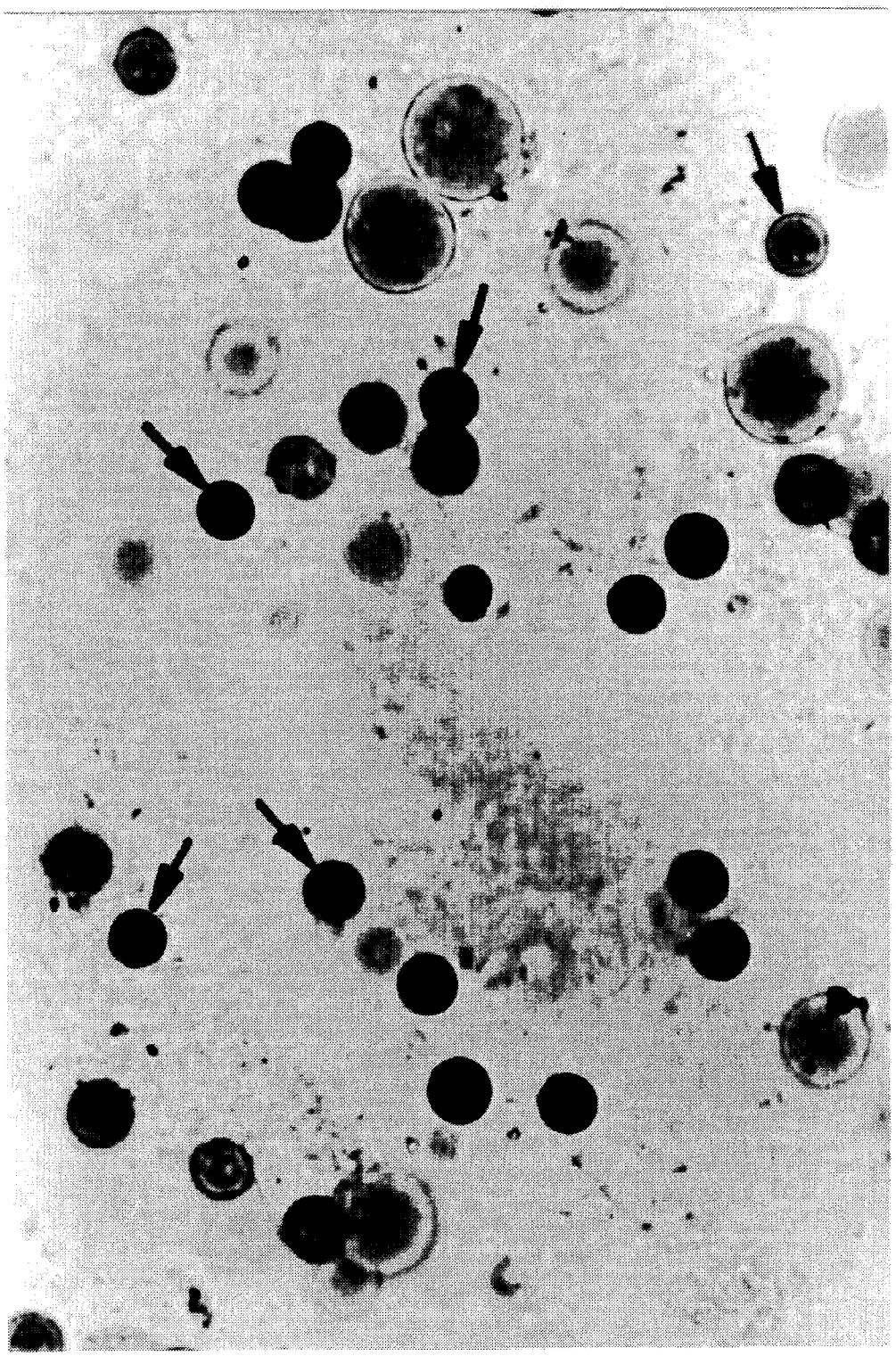
FIG. 6 is a photograph of the zoosporangia and oospores (arrows) of P. rostratum.

One hundred single mutated zoospores that survived the mutagenesis were transferred to 20% V8 ™ juice agar and grown for 10 days at 18° C. Microscopic examination showed no morphological differences except for lack of oospore production in 2 out of 100 isolates (FIGS. 5 and 6). The two mutants were designated (PR4) and (PR24), and have been deposited with the ATCC under ATCC Nos. 20977 and 20978, respectively.

EXAMPLE 4

Host Range Studies

Extensive host range studies were performed using the same experimental protocol as in the initial pathogenicity tests. In this case, however, only 10-day old *P. rostratum* cultures were used, and a more extensive range of plants were studied. As above, the following index rating was used to categorize the extent of disease:

0=no visible damage or root discoloration
1=slight discoloration and root damage
2=extensive root discoloration and/or crown lesions
3=root discoloration and girdling of plant at soil surface
4=death of plant

TABLE 1

Host range studies of *Pythium rostratum* isolate PR1. Results of inoculation involving 38 species within 8 tribes of the Compositae and representative members of the Chenopodiaceae, Cruciferae, Gramineae, Solanaceae and Umbelliferae Inoculated 45 days after planting; Data recorded on day 78.

| Host | FAMILY/TRIBE | MORTALITY (4 WEEKS) | DISEASE RATING |
|---|---|---|---|
| *Beta vulgaris* "beet var. Detroit dark red" | Chenopodiaceae | 0/4 | 0.0 |
| *Achillea millefolium* "yarrow" | Compositae/Anthemis | 0/4 | 0.3 |
| *Artemisia tridentata* "big sagebrush" | Compositae/Anthemis | 0/4 | 0.0 |
| *Chrysanthemum leucanthemu* "oxeye daisy" | Compositae/Anthemis | 0/4 | 0.0 |
| *Solidago canadensis* "Canada goldenrod" | Compositae/Aster | 0/4 | 0.0 |
| *Carduus nutans* "musk thistle" | Compositae/Carduus | 1/4 | 1.3 |
| *Carduus pycnocephalus* "Italian thistle" | Compositae/Carduus | 1/4 | 1.0 |
| *Carduss tenuflorus* "slenderflower thistle" | Compositae/Carduus | 0/4 | 0.0 |
| *Carduus thoermi* "musk thistle" | Compositae/Carduus | 0/4 | 0.0 |
| *Carthamus lanatus* "distaff thistle" | Compositae/Carduus | 0/4 | 0.0 |
| *Centaurea candissima* "dusty-miller" | Compositae/Carduus | 0/4 | 1.0 |
| *Centaurea diffusa* "diffuse knapweed" | Compositae/Carduus | 3/4 | 3.3 |
| *Cirsium ochrocentrum* "yellowspine thistle" | Compositae/Carduus | 3/4 | 3.0 |
| *Cirsium vulgarius* "bull thistle" | Compositae/Carduus | 0/4 | 1.0 |
| *Cichorium endiva* "endive, Green curled | Compositae/Cichorium | 0/4 | 0.0 |
| *Lactuca sativa* "lettuce, Ithaca" | Compositae/Cichorium | 0/4 | 0.3 |
| *Ageratum houstonium* "flossflower" | Compositae/Eupatorium | 0/4 | 0.2 |
| *Gaillardia aristata* "blanket flower" | Compositae/Heleniae | 0/4 | 0.0 |
| *Cosmos sulphureus* "garden cosmos, Mixed colors" | Compositae/Helianthus | 0/4 | 0.0 |
| *Dahlia pinnata* "Common dahlia" | Compositae/Helianthus | 0/4 | 1.0 |
| *Rudbeckia hirta* "black-eyed Susan" | Compositae/Helianthus | 0/4 | 0.0 |
| *Tagetes patula* "marigold, Orange Hawaii" | Compositae/Helianthus | 0/4 | 0.0 |
| *Zinnia elegans* "common zinnia" | Compositae/Helianthus | 0/4 | 0.0 |
| *Anaphalis margaritacea* "pearly everlasting" | Compositae/Inula | 0/4 | 0.0 |
| *Helichrysum bracteatum* "strawflower" | Compositae/Inula | 0/4 | 0.0 |

TABLE 1-continued

Host range studies of *Pythium rostratum* isolate PR1. Results of inoculation involving 38 species within 8 tribes of the Compositae and representative members of the Chenopodiaceae, Cruciferae, Gramineae, Solanaceae and Umbelliferae Inoculated 45 days after planting; Data recorded on day 78.

| Host | FAMILY/TRIBE | MORTALITY (4 WEEKS) | DISEASE RATING |
|---|---|---|---|
| *Brassicaa oleracea* "cabbage, Premium flat Dutch" | Cruciferae | 0/4 | 0.0 |
| *Agropyron dasytachyum* "thickspike wheatgrass" | Gramineae | 0/4 | 0.0 |
| *Agropyron elongatum* "alkar tall wheatgrass" | Gramineae | 0/4 | 0.0 |
| *Agropyron intermedium* "intermediate wheatgrass" | Gramineae | 0/4 | 0.0 |
| *Agrostis alba* "red top" | Gramineae | 0/4 | 0.0 |
| *Bromus inermis* "Manchar smooth bromegrass" | Gramineae | 0/4 | 0.0 |
| *Dactylis glomerata* "orchardgrass" | Gramineae | 0/4 | 0.0 |
| *Elymis cinereus* "basin wild rye" | Gramineae | 0/4 | 0.0 |
| *Festuca arizonica* "Arizona fescue" | Gramineae | 0/4 | 0.0 |
| *Phleum pratense* (climax timothy) | Gramineae | 0/4 | 0.0 |
| *Phleum pratense* (common timothy) | Gramineae | 0/4 | 0.0 |
| *Lycopersicon lycopersium* "tomato, Roma" | Solananceae | 0/4 | 0.0 |
| *Daucus carota* "carrot, Danvers half long" | Umbelliferae | 0/4 | 0.0 |

TABLE 2

Host range studies of *Pythium rostratum* isolate PR1. Results of inoculations involving 53 species of plants within the Betulaceae, Chenopodiaceae, Compositae, Cruciferae, Cucurbitaceae, Ericaceae, Gramineae, Leguminosae, Pinaceae, Rosaceae, Scrophulariaceae, Solanaceae and Umbelliferae. Columns I, II, and III indicate three different experiments recorded 27, 39, and 28 days respectively, after inoculation.

| Host | FAMILY/TRIBE | MONTH AFTER INOCULATION No. DEAD/No. INOC. | | | DR* |
|---|---|---|---|---|---|
| | | I | II | III | |
| *Alnus sinuata* "Sitka alder" | Betulaceae | | 0/4 | | 0.0 |
| *Beta vulgaris* "beet, Detroit dark red" | Chenopodiaceae | 0/4 | | | 0.0 |
| *Achilles lanulosa* "western yarrow" | Comp./Anthemis | 0/4 | | | 0.0 |
| *Achillea Millefolium* "yarrow" | Comp./Anthemis | | | 0/4 | 0.0 |
| *Artemisia ludoviciana* "Louisiana sagewort" | Comp./Anthemis | | 0/4 | 0/4 | 0.3 |
| *Artemisia tridentata* "big sagebrush" | Comp./Anthemis | 0/4 | 0/4 | 0/4 | 0.0 |
| *Chrysanthemum leucanthemun* "oxeye daisy" | Comp./Anthemis | 0/4 | | | 0.0 |
| *Gazania rigens* "treasure flower" | Comp/Arctotis | | 0/4 | | 0.0 |
| *Aster chilensis* "Pacific aster" | Comp./Aster | 0/4 | 0/4 | 0/4 | 0.0 |
| *Solidago canadensis* "Canada goldenrod" | Comp./Aster | 0/4 | | | 0.0 |
| *Calendula officinalis* "pot marigold" | Comp./Calendula | 0/4 | | | 0.0 |
| *Carduus thoermi* "musk thistle" | Comp./Carduus | 0/4 | | | 0.0 |
| *Centaurea candissima* "dusty-miller" | Comp./Carduus | 0/4 | | | 0.8 |
| *Centaurea diffuse* | Comp./Carduus | 2/4 | 3/4 | 2/4 | 3.3 |

TABLE 2-continued

Host range studies of *Pythium rostratum* isolate PR1. Results of inoculations involving 53 species of plants within the Betulaceae, Chenopodiaceae, Compositae, Cruciferae, Cucurbitaceae, Ericaceae, Gramineae, Leguminosae, Pinaceae, Rosaceae, Scrophulariaceae, Solanaceae and Umbelliferae. Columns I, II, and III indicate three different experiments recorded 27, 39, and 28 days respectively, after inoculation.

| Host | FAMILY/TRIBE | MONTH AFTER INOCULATION No. DEAD/No. INOC. | | | |
|---|---|---|---|---|---|
| | | I | II | III | DR* |
| "diffuse knapweed" *Cichorium endica* | Comp./Cichorium | 0/4 | | | 0.0 |
| "endive, Greed curled" *Lactuca sativa* | Comp./Cichorium | 0/4 | | | 0.0 |
| "lettuce, Ithaca" *Ageratum houstonium* | Comp./Eupatorium | 0/4 | | | 0.0 |
| "Flossflower" *Gaillardia aristata* | Comp./Heleniae | 0/4 | | 0/4 | 0.0 |
| "blanket flower" *Coreopsis lanceolata* | Comp./Helianthus | 0/4 | 0/4 | | 0.0 |
| "tickseed" *Cosmos sulphureus* | Comp./Helianthus | 0/4 | | | 0.3 |
| "garden cosmos, Mixed colors" *Dahlia pinnata* | Comp./Helianthus | 0/4 | | | 0.0 |
| "common dahlia" *Echinacea purpurea* | Comp./Helianthus | | 0/4 | | 0.0 |
| "purple coneflower" *Helianthus maximilianii* | Comp./Helianthus | | | 0/4 | 0.0 |
| "Maximillian sunflower" *Ratibida columnaris* | Comp./Helianthus | | 0/4 | | 0.0 |
| "prairie coneflower" *Rudbeckia hirta* | Comp./Helianthus | 0/4 | | | 0.0 |
| "black-eye Susan," *Tagetes patula* | Comp./Helianthus | 0/4 | | | 0.0 |
| "marigold, Orange Hawaii" *Zinnia elegans* | Comp./Helianthus | | 0/4 | | 0.0 |
| "common zinnia" *Anaphalis margaritacea* | Comp./Inula | 0/4 | | 0/4 | 0.0 |
| "pearly everlasting" *Helichrysum bracteatum* | Comp./Inula | 0/4 | | | 0.0 |
| "strawflower" *Brassica oleracea* | Cruciferae | 0/4 | | | 0.0 |
| "cabbage, Premium flat Dutch" *Cucurbita moschata* | Cucurbitaceae | 0/4 | | | 0.0 |
| "winter squash, Waltham butternut" *Vaccinium membranaceum* | Ericaceae | 0/4 | | | 0.0 |
| "Black mountain huckleberry" *Agropyron dasystachyum* | Gramineae | 0/4 | | 0/4 | 0.0 |
| "thickspike wheatgrass" *Agropyron desertorum* | Gramineae | 0/4 | | 0/4 | 0.0 |
| "standard crested wheatgrass" *Agropyron elongatum* | Gramineae | 0/4 | | 0/4 | 0.0 |
| "Alkar tall wheatgrass" *Agropyron intermedium* | Gramineae | 0/4 | | 0/4 | 0.0 |
| "intermdiate wheatgrass" *Agropyron spicatum* | Gramineae | | | 0/4 | 0.0 |
| "bluebunch wheatgrass" *Agrostis alba* | Gramineae | | | 0/4 | 0.0 |
| "redtop" *Bromus inermis* | Gramineae | 0/4 | | 0/4 | 0.0 |
| "Manchar smooth brome grass" *Dactylis glomerata* | Gramineae | 0/4 | | 0/4 | 0.0 |
| "orchardgrass" *Elymus cinereus* | Gramineae | 0/4 | | 0/4 | 0.0 |
| "basin wild rye" *Festuca arizonica* | Gramineae | 0/4 | | 0/4 | 0.0 |
| "Arizona fescue" *Phleum pratense* | Gramineae | 0/4 | | 0/4 | 0.0 |
| "common timothey, Climax" *Phleum pratense* | Gramineae | 0/4 | | 0/4 | 0.0 |
| "common timothy" *Poa compressa* | Gramineae | 0/4 | | 0/4 | 0.0 |
| "Canada bluegrass" *Zea mays* | Gramineae | | 0/4 | | 0.0 |
| "sweet corn, Indian chief" *Robina psuedoacacia* | Leguminosae | | | 0/4 | 0.0 |
| "black locust" | | | | | |

TABLE 2-continued

Host range studies of *Pythium rostratum* isolate PR1. Results of inoculations involving 53 species of plants within the Betulaceae, Chenopodiaceae, Compositae, Cruciferae, Cucurbitaceae, Ericaceae, Gramineae, Leguminosae, Pinaceae, Rosaceae, Scrophulariaceae, Solanaceae and Umbelliferae. Columns I, II, and III indicate three different experiments recorded 27, 39, and 28 days respectively, after inoculation.

| Host | FAMILY/TRIBE | I | II | III | DR* |
|---|---|---|---|---|---|
| *Pinus contorta* "lodgepole pine" | Pinaceae | | | 0/4 | 0.0 |
| *Pseudotsuga menzesii* "Douglas fir" | Pinaceae | | | 0/4 | 0.0 |
| *Holodiscus discolor* "creambush oceanspray" | Rosaceae | | 0/4 | | 0.0 |
| *Castilleja sp.* "indian paintbrush" | Scrophulariaceae | | 0/4 | | 0.0 |
| *Lycopersicon lycopersicum* "tomato, Roma" | Solanaceae | | 0/4 | | 0.0 |
| *Daucus carota* "carrot, Danvers half long" | Umbelliferae | 0/4 | | | 0.0 |

*Disease rating

TABLE 3

Pathogenicity of *Pythium rostratum* original isolate (PR1) on susceptible Compositae, compared to two, non-oospore producing biochemical mutants (PR4 and PR24) created from PR1. Data recorded 29 days after inoculation.

| Host | TRIBE | PLANT KILL 4 wk | | | | DISEASE RATING | | | |
|---|---|---|---|---|---|---|---|---|---|
| | | C* | 1 | 4 | 24 | C | 1 | 4 | 24 |
| *Achillea millefolium* "yarrow" | Anthemis | 0/4 | 0/4 | 0/4 | 0/4 | 0.0 | 0.3 | 0.0 | 0.3 |
| *Carduus pycnocephalus* "Italian thistle" | Carduus | 0/4 | 0/4 | 0/4 | 0/4 | 0.0 | 1.0 | 1.8 | 2.3 |
| *Carthamus tinctorius* "safflower, S-541" | Carduus | 0/4 | 0/4 | 0/4 | 0/4 | 0.0 | 1.3 | 1.0 | 1.3 |
| *C. tinctorius* "safflower, Pacific 1" | Carduus | 0/4 | 0/4 | 0/4 | 0/4 | 0.0 | 2.0 | 1.3 | 1.5 |
| *Centaurea diffusa* "diffuse knapweed" | Carduus | 0/4 | 0/4 | 1/4 | 2/4 | 0.0 | 1.8 | 2.0 | 3.0 |
| *C. calcitrapa* "purple starthistle" | Carduus | 0/4 | 0/4 | 0/4 | 0/4 | 0.0 | 0.8 | 0.5 | 1.5 |
| *C. macrocephala* "bighead knapweed" | Carduus | 0/4 | 0/4 | 0/4 | 0/4 | 0.0 | 1.5 | 0.5 | 1.5 |
| *C. maculosa* "spotted knapweed" | Carduus | 0/4 | 0/4 | 0/4 | 0/4 | 0.0 | 1.5 | 0.6 | 1.0 |
| *C. melitensis* "Napa thistle" | Carduus | 0/4 | 0/4 | 0/4 | 0/4 | 0.0 | 0.3 | 0.5 | 0.5 |
| *C. rothrockii* "basketflower" | Carduus | 0/4 | 1/4 | 0/4 | 1/4 | 0.0 | 2.5 | 0.5 | 1.5 |
| *C. solstitialis* "yellow starthistle" | Carduus | 0/4 | 0/4 | 0/4 | 0/4 | 0.0 | 1.5 | 0.5 | 1.0 |
| *C. sulphurea* "Sicilian knapweed" | Carduus | 0/4 | 0/4 | 0/4 | 0/4 | 0.0 | 1.0 | 1.0 | 1.3 |
| *Cynara scolymus* "artichoke" | Carduus | 0/4 | 1/4 | 0/4 | 0/4 | 0.0 | 1.5 | 1.5 | 1.8 |
| *lactuca sativa* "lettuce, Ithaca" | Cichorium | 0/4 | 0/4 | 0/4 | 0/4 | 0.0 | 0.0 | 0.5 | 0.8 |
| *Ageratum houstonium* "flossflower" | Eupatorium | 0/4 | 0/4 | 0/4 | 0/4 | 0.0 | 0.0 | 0.0 | 0.5 |
| *Dahlia pinnata* "common dahlia" | Helianthus | 0/4 | 0/4 | 0/4 | 0/4 | 0.0 | 1.3 | 1.0 | 1.8 |

C) control / uninoculated, 1) inoculated with PR1, 4) inoculated with PR4, 24) inoculated with PR24.

TABLE 4

Pathogenicity of *Pythium rostratum* original isolate from Geneva,
Switzerland (PR1) on susceptible Compositae, compared to two, non-oospore
producing biochemical mutants (PR4 and PR24) created from PR1. Data
recorded 28 days after inoculation.

| Host | TRIBE | PLANT KILL 4 wk | | | | DISEASE RATING | | | |
|---|---|---|---|---|---|---|---|---|---|
| | | C* | 1 | 4 | 24 | C | 1 | 4 | 24 |
| *Achillea millefolium* "yarrow" | Anthemis | 0/4 | 0/4 | 0/4 | 0/4 | 0.0 | 0.5 | 0.3 | 0.0 |
| *Achillea tinctorius* "safflower, S-541 | Carduus | 0/4 | 0/4 | 0/4 | 0/4 | 0.0 | 1.0 | 1.0 | 1.0 |
| *C. tinctorius* "safflower. Pacific 1" | Carduus | 0/4 | 0/4 | 0/4 | 0/4 | 0.0 | 1.0 | 1.0 | 1.0 |
| *Centaurea diffusa* "diffuse knapweed" | Carduus | 0/4 | 3/4 | 3/4 | 2/4 | 0.0 | 3.8 | 3.3 | 3.0 |
| *C. americana* "basket-flower" | Carduus | 0/4 | 2/4 | 3/4 | 2/4 | 0.0 | 2.5 | 3.3. | 2.8 |
| *C. calcitrapa* "purple starthistle" | Carduus | 0/4 | 0/4 | 0/4 | 2/4 | 0.0 | 0.8 | 0.5 | 2.5 |
| *C. candissima* "dusty-miller" | Carduus | 0/4 | 1/4 | 0/4 | 0/4 | 0.0 | 1.3 | 1.5 | 0.5 |
| *C. debauxii* "meadow knapweed" | Carduus | 0/4 | 0/4 | 0/4 | 0/4 | 0.0 | 0.3 | 1.0 | 0.0 |
| *C. gymnocarpa* "dusty-miller" | Carduus | 0/4 | 0/4 | 0/4 | 1/4 | 0.0 | 1.5 | 0.8 | 1.8 |
| *C. repens* "Russian knapweed" | Carduus | 0/4 | 1/4 | 1/4 | 0/4 | 0.0 | 2.0 | 2.3 | 1.5 |
| *C. Squarrosa* "squarrose knapweed" | Carduus | 0/4 | 2/4 | 3/4 | 1/4 | 0.0 | 2.5 | 3.3 | 3.0 |
| *C. sulphurea* "Sicilian knapweed" | Carduus | 0/4 | 0/4 | 0/4 | 0/4 | 0.0 | 1.0 | 1.0 | 1.0 |
| *Cynara scolymus* "artichoke" | Carduus | 0/4 | 1/4 | 0/4 | 0/4 | 0.0 | 1.5 | 1.5 | 1.8 |
| *Ageratum houstonium* "flossflower" | Eupatorium | 0/4 | 0/4 | 0/4 | 0/4 | 0.0 | 0.8 | 0.0 | 0.0 |

*C) control / uninoculated, 1) inoculated with PR1, 4) inoculated with PR4, 24) inoculated with PR24.

In summary, 59 species of plants from 12 families (Betulaceae, Chenopodiaceae, Cruciferae, Cucurbitaceae, Ericaceae, Gramineae, Leguminosae, Pinaceae, Rosaceae, Scrophulariaceae, Solanaceae and Umbelliferae) and 10 Tribes of the Compositae (Anthem is, Arctotis, Aster, Calendula, Carduus, Cichorium Eupatorium, Heleniae, Helianthus and Inula) were inoculated with cultures of PR-1. Results showed high susceptibility to this pathogen only in Compositae in the Carduus tribe. In these tests, *Centaurea diffusa*, with plant mortality rates of 50%–75%, was a highly susceptible species. *Cirsium ochrocentrum* was also extremely susceptible, with 75% mortality; *Carduus nutans* and *C. pycnocephalus* showed low susceptibility, with 25% plant mortality. *Centaurea candissima* and *Cirsium vulgaris* in the Carduus tribe showed root rot with dark brown discoloration but no plant death. *Dahlia pinnata* in the Helianthus tribe was the only plant species out of the Carduus tribe that was found to be a host to this pathogen (see Tables 1 and 2).

Subclinical root infection was evident in *Achillea millefolium* and *Artemisia ludoviciana*, Anthemis tribe, *Lactuca sativa*, Cichorium Tribe, *Ageratum houstonium*, Eupatorium Tribe, and *Cosmos sulphureus*, Helianthus tribe (see Tables 1 and 2). These plant species showed a 0.3 disease index.

Other host range studies were performed in order to compare the host range of the original isolate of *P. rostratum* (PR1) with the two non-oosporeproducing biochemical mutants (PR4 and PR24). This study indicated that the biochemical mutants did not differ greatly in pathogenicity from the original isolate, PR1.

Noticeable feeder root infection accompanied by dark brown lesions in large roots was noticed in all members of the Carduus tribe used in this test. Plant mortality with a similar disease index occurred in *Centaurea diffusa*, *C. americana*, and *C. squarrosa* inoculated with PR1, PR4, and PR24. However, PR1 caused plant death in *C. rothrockii* and *Cynara scolymus*, and PR24 killed one *C. rothrockii* plant. PR4 did not kill any of the test plants. However, the disease index for all these species was very similar (see Tables 3 and 4).

*Dahlia pinnata* in the Helianthus tribe was susceptible to all isolates in similar degree and had a disease index >1.0. Subclinical feeder root infection with 0.3–0.8 disease index was shown by *Achillea millefolium*, Anthemis tribe, *Ageratum houstonium*, Eupatorium tribe, *Centaurea melitensis*, Carduus tribe, and *Lactuca sativa*, Cichorium tribe (see Tables 3 and 4).

EXAMPLE 5

Application of *Pythium rostratum* To
Knapweed-infested Land

A carrier is first prepared for delivery of *P. rostratum*. One percent by weight of $CaCO_3$ is added to 82% by weight V8 ™ juice. $CaCO_3$ is used to increase the alkalinity of the V8™ juice into the range of pH 6.4 to 6.6. The V8™ juice/$CaCO_3$ is then added to 17% by weight vermiculite in order to completely saturate the vermiculite. The V8 ™ juice/$CaCO_3$ -saturated vermiculite constitutes the carrier, and is steam sterilized at 20 pounds of pressure for 20 minutes. *P. rostratum* is then inoculated into the carrier and grown for 20 days at 25° C., so that zoosporangia may be produced.

After 20 days, the carrier with abundant zoosporangia and mycelium of the growing *P. rostratum* is applied to the land infected with knapweed. The soil is 100% of its moisture capacity, and the temperature ranges from 8 to 18° C. The carrier is delivered to the land infested with knapweed with a manual fertilization spreader. The rate of inoculation is about 28,000 zoosporangia/ft$^2$.

I claim:

1. A method for selectively killing knapweed, comprising:
   (a) growing *Pythium rostratum* which selectively kills knapweed on a carrier saturated with a liquid nutrient capable of supporting *Pythium rostratum* growth and the production of zoosporangia; and
   (b) applying the *Pythium rostratum* carrier to knapweed-infested land under moisture and temperature conditions sufficient to support *Pythium rostratum* growth and zoospore release by the zoosporangia, said zoospores being capable of killing knapweed.

2. The method of claim 1 wherein said carrier comprises vermiculite, juice which contains extracts of eight different vegetables, CaCO$_3$.

3. The method of claim 2 wherein said carrier consists of about 17% by weight vermiculite, about 82% by weight vegetable juice, and about 1% by weight CaCO$_3$.

4. The method of claim 1 wherein the carrier is applied under moisture conditions of approximately 100% of soil capacity.

5. The method of claim 1 wherein the carrier is applied under temperature conditions of about 8° C. to 18° C.

6. A composition suitable for application to knapweed infested land, comprising,
   (a) a culture of *Pythium rostratum*, said culture being capable of producing zoosporangia which produce zoospores capable of killing knapweed; and
   (b) a carrier saturated with a liquid nutrient capable of supporting *Pythium rostratum* growth and the production of zoosporangia.

7. The composition of claim 6 wherein said culture of *Pythium rostratum* has been mutagenized such that oospores are not produced.

8. The composition of claim 6 wherein said carrier comprises vermiculite, vegetable juice, and CaCO$_3$.

9. The composition of claim 8 wherein said carrier consists of about 17% by weight vermiculite, about 82% by weight vegetable juice, and about 1% by weight CaCO$_3$.

* * * * *

UNITED STATES PATENT AND TRADEMARK OFFICE
CERTIFICATE OF CORRECTION

PATENT NO. : 5,455,219
DATED : Oct. 3, 1995
INVENTOR(S) : Eduardo E. Trujillo

It is certified that error appears in the above-indentified patent and that said Letters Patent is hereby corrected as shown below:

In column 19, claim 2, line 25, after "vegetables," and before "$CaCO_3$", please insert --and--.

Signed and Sealed this

Thirtieth Day of January, 1996

Attest:

BRUCE LEHMAN

*Attesting Officer*   Commissioner of Patents and Trademarks